(12) United States Patent
Park et al.

(10) Patent No.: US 11,202,751 B2
(45) Date of Patent: Dec. 21, 2021

(54) **WHITENING COSMETIC COMPOSITION COMPRISING *CARAGANA SINICA* ROOT EXTRACT**

(71) Applicants: CELLTRION, INC., Incheon (KR); COSEEDBIOPHARM CO., LTD., Chungcheongbuk-do (KR)

(72) Inventors: Sung Min Park, Chungcheongbuk-do (KR); Jung No Lee, Chungcheongbuk-do (KR); Hyo Min Kim, Jeju-do (KR); Jae Mun Kim, Chungcheongbuk-do (KR); Kwang Jun Yoon, Incheon (KR); Seung Ki Lee, Incheon (KR); Jae Hun Kim, Gyeonggi-do (KR); Yeon Sook Kim, Gyeonggi-do (KR); Joo Hyuck Lim, Incheon (KR); Heyong Mi Kim, Gyeonggi-do (KR); Sung Ho Moon, Gyeonggi-do (KR)

(73) Assignees: CELLTRION INC., Incheon (KR); COSEEDBIOPHARM CO., LTD., Chungcheongbuk-Do (KR)

( * ) Notice: Subject to any disclaimer, the term of this patent is extended or adjusted under 35 U.S.C. 154(b) by 0 days.

(21) Appl. No.: 15/740,748

(22) PCT Filed: Jun. 29, 2016

(86) PCT No.: PCT/KR2016/006983
§ 371 (c)(1),
(2) Date: Dec. 28, 2017

(87) PCT Pub. No.: WO2017/003190
PCT Pub. Date: Jan. 5, 2017

(65) Prior Publication Data
US 2018/0185269 A1    Jul. 5, 2018

(30) Foreign Application Priority Data
Jun. 30, 2015  (KR) .................. 10-2015-0092848

(51) Int. Cl.
| | | |
|---|---|---|
| *A61Q 19/00* | (2006.01) | |
| *A61K 8/96* | (2006.01) | |
| *A61Q 19/02* | (2006.01) | |
| *A61K 31/343* | (2006.01) | |
| *A61K 36/48* | (2006.01) | |
| *A61K 8/9789* | (2017.01) | |
| *A61P 17/02* | (2006.01) | |
| *A61K 8/49* | (2006.01) | |

(52) U.S. Cl.
CPC .............. *A61K 8/96* (2013.01); *A61K 8/4973* (2013.01); *A61K 8/9789* (2017.08); *A61K 31/343* (2013.01); *A61K 36/48* (2013.01); *A61P 17/02* (2018.01); *A61Q 19/02* (2013.01)

(58) Field of Classification Search
CPC ........ A61K 8/96; A61K 8/4976; A61K 36/48; A61K 31/343; A61K 8/97; A61K 8/49; A61P 17/02; A61Q 19/02; A61Q 19/00
See application file for complete search history.

(56) References Cited

FOREIGN PATENT DOCUMENTS

| CN | 1132597 | 10/2000 |
|---|---|---|
| CN | 100584837 C | 1/2010 |
| FR | 2 844 715 A1 | 3/2004 |
| FR | 2 929 850 A1 | 10/2009 |
| KR | 20030084271 | 11/2003 |
| KR | 100870263 | 11/2008 |
| KR | 20080104759 | 12/2008 |
| KR | 20080104759 A | * 12/2008 |

OTHER PUBLICATIONS

Resverad (Caragana Sinica Ferment Extract) Purpose for Whitening Agent. 2009 (multiple studies were made during the year 2009 and finished 2010 (Year: 2010).*
Prakash et al., Multifunctional Skin Tone Lighteners from Nature: An Overview Euro Cosmetics Jun. 2009, p. 19-23 (Year: 2009).*
Kim et al., Stilbene Derivatives as Human 5-HT6 Receptor Antagonist from the Root of Caragana Sinica, 2010 Pharmaceutical Society of Japan. (Year: 2010).*
Kittisak, Stilbenes with tyrosinase inhibitory activity, Current Science, vol. 94, No. 1, Jan. 10, 2008. (Year: 2008).*
Jin et al., Antioxidative oigostilbenes from Caragana sinica, Bioorganic & Medicinal Chemistry Letters 22 (2012) 973-976. (Year: 2012).*
Xue et al., Resveratrol Oligomers for the Prevention and Treatment of Cancers, Oxidative Medicine and Cellular Longevity, vol. 2014, Article ID 765832, 9 pages. (Year: 2014).*
Kim et al., Screening of plant extracts for human tyrosinase inhibiting effects, International Journal of Cosmetic Science, 2012, 34, 202-208. (Year: 2012).*
Cheng et al., A new tetrastilbene from Caragana Sinica, Chinese Chemical Letters 19 (2008) 711-715. (Year: 2008).*
Kitanaka, S. et al., "(+)-α-Viniferin, an Anti-inflamatory Compound from *Caragana chamlagu* Root," Chem. Pharm. Bull., 38:432-435, Pharmaceutical Society of Japan (1990).

(Continued)

*Primary Examiner* — Susan T Tran
(74) *Attorney, Agent, or Firm* — Potomac Law Group, PLLC (57) ABSTRACT

The present invention relates to a cosmetic composition for whitening comprising a *Caragana sinica* root extract, and more specifically relates to a cosmetic composition having an outstanding skin-whitening effect, the composition comprising a *Caragana sinica* root extract, a fraction thereof or α-viniferin isolated therefrom. In the present invention, the *Caragana sinica* root extract, fraction thereof or α-viniferin isolated therefrom inhibits tyrosinase activity and suppresses melanin production and is therefore effective in skin whitening.

2 Claims, 4 Drawing Sheets

(56) References Cited

OTHER PUBLICATIONS

English Translation of International Search Report of PCT/KR206/006983, WIPO (dated Oct. 20, 2016).
Extended European Search Report dated Feb. 6, 2019, in corresponding European Application No. 16818223.6 (12 pages, in English).

* cited by examiner

WHITENING COSMETIC COMPOSITION COMPRISING *CARAGANA SINICA* ROOT EXTRACT

TECHNICAL FIELD

The present invention relates to a cosmetic composition comprising a *Caragana Sinica* root extract, a fraction thereof or α-viniferin isolated therefrom, such that an excellent skin whitening effect is achieved.

BACKGROUND

A melanism of skin is generally caused by a reaction of skin cells to internal and external factors, in particular wherein one representative factor is an exposure of skins to ultraviolet (UV) rays. In other words, if the skin is exposed to UV rays, a tyrosinase is activated, which acts on a tyrosine, a kind of amino acid present in skin tissues, to produce a dopa. After this, a polymer, called melanin, is synthesized from a melanosome in a melanocyte, i.e. skin pigment cell, through an oxidation process for producing a dopaquinone. This melanin is transferred to a keratinocyte, which is a keratin-forming cell of skin, and then reaches a skin surface by means of a keratinization process, such that the skin is protected from the UV rays.

The melanin is an UV protector indispensable to human body, and plays a role as a free radical scavenger effective in scavenging various radicals which convert biocomponents such as protein, lipid, nucleic acid, etc. However, if the melanin is locally and excessively synthesized, or the skin's physiological functions deteriorate due to skin lesions and aging, the melanin is deposited onto a skin surface to cause melasma, freckle, and various pigmentations.

As a cause and mechanism of such skin melanism has been found out, methods for blending cosmetics with substances having an inhibitory effect on the activity of the tyrosinase involved in a skin melanism process, or for reducing a production of the melanin by inhibiting a part of reactions during a melanin production process, have been generally used to prevent the skin melanism. As a representative substance used for such purpose, there are arbutin, ascorbic acid and hydroquinone, wherein plant extracts therefor are a mulberry root extract, licorice extract, etc.

The arbutin acts on excellently inhibiting the activity of the tyrosinase, but has a problem with stability such as a titer decrease caused by a change with passage of time, as well as a discoloration upon its blending with cosmetics, and also has a high skin irritation, such that its use is limited. The ascorbic acid has a low inhibitory effect on the activity of the tyrosinase and its molecule per se has a low stability, so there is a problem in that the ascorbic acid is not appropriate as a melanin production inhibitor. The hydroquinone has a problem with stability due to its high irritation to the skin, so there is now a problem in that usability thereof is limited when being blended for cosmetics. Also, most of plant extracts have a problem such as showing a comparatively high inhibitory effect on the activity of the tyrosinase only at a high concentration, and showing almost no inhibitory effect at a low concentration. In particular, existing melanin production inhibitors have the biggest problem in that they show an insignificant whitening effect at a clinical experiment on actual human skins.

DETAILED DESCRIPTION OF THE INVENTION

Technical Problem

Accordingly, the present inventors conducted a study to solve a problem of natural plant material extracts, such that the present inventors identified an excellent whitening efficacy from a *Caragana Sinica* root extract, a fraction thereof or α-viniferin isolated therefrom and completed the present invention.

Thus, an object to be solved by the present invention is to provide a cosmetic composition for whitening, comprising a *Caragana Sinica* root extract, a fraction thereof or α-viniferin isolated therefrom as an active ingredient.

Also, another object to be solved by the present invention is to provide a skin whitening method comprising a step of applying the above cosmetic composition to skin.

Furthermore, yet another object to be solved by the present invention is to provide a pharmaceutical composition for preventing or treating a melanin hyperpigmentation disease, comprising a *Caragana Sinica* root extract, a fraction thereof or α-viniferin isolated therefrom as an active ingredient.

Technical Solution

To solve the above objects, the present invention provides a cosmetic composition for whitening, comprising a *Caragana Sinica* root extract, a fraction thereof or α-viniferin isolated therefrom as an active ingredient.

Also, the present invention provides a skin whitening method comprising a step of applying the above cosmetic composition to skin.

Furthermore, the present invention provides a pharmaceutical composition for preventing or treating a melanin hyperpigmentation disease, comprising a *Caragana Sinica* root extract, a fraction thereof or α-viniferin isolated therefrom as an active ingredient.

Hereinafter, the present invention will be described in more detail.

The present invention provides a cosmetic composition for whitening, comprising a *Caragana Sinica* root extract, a fraction thereof or α-viniferin isolated therefrom as an active ingredient.

The *Caragana Sinica*, as a perennial, deciduous broad-leaved shrub plant, is characterized by showing whiter color compared to other closely related plants and is also referred to as Chinese pea shrub, Chinese pea tree, *Cytisus scoparius, Sarothamnus scoparius*, broom, scotch broom, genista, etc. The *Caragana Sinica* grows wild at an altitude of 400 m or less in a vertical aspect, as well as in Korea's various regions such as Jeonbuk, Gyeongnam, Chungnam, Gyeonggi, etc., in a horizontal aspect, and also it is planted around villages. This plant is 2 m high, wherein a bunch of branches grow from a stem. It has a pinnate compound leaf with two pairs of leaf attached to each other and grows in alternation, wherein an end of leaf generally consists of a thorn and has four leaflets, which are thick and take on an obovoid or oval form. A leaf is 1 to 3 cm long, and a surface thereof is dark green and glossy, while a back side thereof is greenish gray, having no down. A petiole is 4 to 8 mm long and turns into a thorn. A branch facing upward grows, extending in all directions, wherein the branch has 5 ridges, takes on a grayish brown color and has no down. There are thorns all around and rootlets grow long. A flower, which takes on a butterfly shape and a yellowish color, brooms in May one by one in a racemous inflorescence manner. A flower stalk is about 1 cm long and has one node at a center thereof. Its flower cup takes on a bell shape with some brown downs. Its legume is 3 to 3.5 cm long, takes on a cylindrical shape without any downs, and grows ripe in September, but hardly reaches fructification.

The extract may be obtained by extracting a *Caragana Sinica* root with water, $C_1$ to $C_4$ lower alcohols or a mixed solvent thereof, wherein these lower alcohols may be ethanol or methanol, and more particularly ethanol.

In one embodiment of the present invention, it was identified that an ethanol extract of *Caragana Sinica* root inhibits the activity of tyrosinase and inhibits a production of melanin, thereby exhibiting excellent skin-whitening effect.

The extract, fraction or α-viniferin may be contained in 0.001 wt % to 30 wt %, more particularly contained in 0.01 wt % to 10 wt %, based on the total weight of the composition. In case that a content of the extract, fraction or α-viniferin is less than 0.001 wt %, there does not occur skin-whitening improvement effect, and in case of exceeding 30 wt %, a degree of increasing skin-whitening improvement effect is insignificant with regard to a content increase, as well as there is a problem with safety and stability of formulation, and not economical.

The fraction of *Caragana Sinica* root extract may be obtained by adding an organic solvent selected from the group consisting of hexane, chloroform, ethyl acetate and butanol, more particularly by adding ethyl acetate, but is not limited thereto.

In one embodiment of the present invention, it was identified that a hexane fraction, a chloroform fraction, an ethyl acetate fraction and a butanol fraction, which are obtained from a *Caragana Sinica* root extract, inhibit the activity of tyrosinase and inhibit the production of melanin, thereby exhibiting excellent skin-whitening effect, and confirmed that the ethyl acetate fraction shows more excellent whitening effect.

The fraction of *Caragana Sinica* root extract may contains 0.001 wt % to 30 wt % of α-viniferin based on the total weight of the fraction, more specifically may contains 0.01 wt % to 10 wt %, and even more specifically may contains 0.1 wt % to 1 wt %.

The α-viniferin has a structure represented by the following Formula 1.

[Formula 1]

In the present invention, the *Caragana Sinica* root extract or the fraction thereof may be prepared by a preparing method comprising following steps, but is not limited thereto:

1) Adding an extraction solvent to a *Caragana Sinica* root to extract;
2) Filtering the extract of the step 1);
3) Concentrating the filtered extract of a step 2) under reduced pressure, followed by drying; and
4) Adding an organic solvent to the dried extract of the step 3) to prepare a fraction of *Caragana Sinica* root.

In the above method, the *Caragana Sinica* root of the step 1) may be used without limitation such as a cultivated one, a commercially available one or the like.

In the above method, an extraction method for the *Caragana Sinica* root extract may be a conventional method in the art, such as filtration method, hot water extraction, immersion extraction, reflux cooling extraction, ultrasonic extraction, supercritical extraction, etc., and the extract may be prepared under a conventional condition of temperature and pressure known in the art. Also, the extract may be obtained in such a way that it is extracted by water, $C_1$ to $C_4$ lower alcohols or a mixed solvent thereof used as an extraction solvent, and these lower alcohols may be ethanol or methanol. The extract may be obtained by adding the extraction solvent that amounts to 1 to 20 times of a quantity of a dried *Caragana Sinica* root, specifically 5 to 15 times thereof, but is not limited thereto. Also, an extraction temperature may be 20 to 70° C., specifically 25 to 65° C., and more specifically 30 to 60° C., but is not limited thereto. Furthermore, an extraction time may be 1 to 20 hours, specifically 2 to 15 hours, but is not limited thereto.

In the above method, the extract of *Caragana Sinica* root of the step 2) may be filtered 1 to 5 times, but is not limited thereto.

In the above method, the concentration under reduced pressure of the step 3) may use a vacuum decompression concentrator or a vacuum rotary evaporator, but is not limited thereto. Also, the drying may be decompression drying, vacuum drying, boiling drying, spray drying or freeze drying, but is not limited thereto.

In the above method, the organic solvent of the step 4) may be hexane, chloroform, ethyl acetate, butanol or water, but is not limited thereto. The above fraction may be one of the hexane fraction, the chloroform fraction, the ethyl acetate fraction, the butanol fraction or the water fraction, more specifically the ethyl acetate fraction, which is respectively obtained by fractionating the extract of *Caragana Sinica* root with hexane, chloroform, ethyl acetate, butanol or water. This fraction may be concentrated under reduced pressure after fractionation.

In one embodiment of the present invention, the present invention may be prepared by a method for preparing the fraction of *Caragana Sinica* root extract comprising α-viniferin, wherein the method comprises following steps:

(a) Extracting a pulverized *Caragana Sinica* root with water, $C_1$ to $C_4$ lower alcohols or a mixed solvent thereof;
(b) Fractionating the extract by an organic solvent selected from the group consisting of hexane, chloroform, ethyl acetate and butanol; and
(c) Isolating α-viniferin from the fraction.

A cosmetic composition of the present invention may contain ingredients conventionally used in a cosmetic composition, wherein as an example for these ingredients, this may include conventional adjuvants such as an antioxidant, a stabilizer, a solubilizer, a vitamin, a pigment and a flavoring, as well as a carrier.

The cosmetic composition of the present invention may be prepared as any formulation conventionally prepared in the art, wherein as an example for the cosmetic composition, this may be formulated into solution, suspension, emulsion, paste, gel, cream, lotion, powder, soap, surfactant-containing cleansing, oil, powder foundation, emulsion foundation, wax foundation, pack, massage cream, spray, and the like, but is not limited thereto. More specifically, the cosmetic composition may be prepared as a formulation such as skin lotion, nutrition lotion, nutrition cream, massage cream, essence, eye cream, cleansing cream, cleansing foam, cleansing water, pack, spray or powder.

In the cosmetic composition of the present invention, if a formulation is paste, cream or gel, animal oil, vegetable oil, wax, paraffin, starch, tragacanth, cellulose derivative, polyethylene glycol, silicon, bentonite, silica, talc, zinc oxide or the like may be used as a carrier ingredient.

In the cosmetic composition of the present invention, if a formulation is solution or emulsion, solvent, solubilizer or emulsifier are used as a carrier ingredient, wherein as an example for the carrier ingredient, water, ethanol, isopropanol, ethyl carbonate, ethyl acetate, benzyl alcohol, benzyl benzoate, propylene glycol, 1,3-butylene glycol oil, glycerol aliphatic ester, polyethylene glycol or sorbitan fatty acid ester may be used as a carrier ingredient.

In the cosmetic composition of the present invention, if a formulation is a suspension a liquid-phase diluent such as water, ethanol or propylene glycol, a suspending agent such as ethoxylated isostearyl alcohol, polyoxyethylene sorbitol ester and polyoxyethylene sorbitan ester, microcrystalline cellulose, aluminum metahydroxide, bentonite, agar, tragacanth or the like may be used as a carrier ingredient.

In the cosmetic composition of the present invention, if a formulation is powder or spray, lactose, talc, silica, aluminum hydroxide, calcium silicate or polyamide powder may be used as a carrier ingredient, and specifically, in case of being spray, the cosmetic composition may further contain a propellant such as chlorofluorohydrocarbon, propane/butane or dimethyl ether.

In the cosmetic composition of the present invention, if a formulation is a surfactant-containing cleansing, aliphatic alcohol sulfate, aliphatic alcohol ether sulfate, sulfosuccinate monoester, isethionate, imidazolinium derivative, sarcosinate, fatty acid amid ether sulfate, alkyl amido betaine, aliphatic alcohol, fatty acid glyceride, fatty acid diethanol amide, vegetable oil, lanolin derivative, ethoxylated glycerol fatty acid ester, or the like may be used as a carrier ingredient.

In the cosmetic composition of the present invention, if a formulation is a surfactant-containing cleansing formulation, a surfactant-free cleansing formulation or soap, the cosmetic composition may be wiped out, torn off or washed away with water, after applied to skin. As an example, the soap may be liquid soap, powder soap, solid soap and oil soap, and the surfactant-containing cleaning formulation may be cleansing foam, cleansing water, cleansing towel and cleansing pack, and the surfactant-free cleansing formulation may be cleansing cream, cleansing lotion, cleansing water and cleansing gel, but are not limited thereto.

The cosmetic composition of the present invention may be redundantly used with other cosmetic compositions than that of the present invention. Also, the cosmetic composition according to the present invention may be used according to a conventional method of use, and the number of uses thereof may be subject to change depending on a user's skin condition or taste.

The cosmetic composition according to the present invention comprises a *Caragana Sinica* root extract comprising α-viniferin, a fraction thereof, or α-viniferin isolated therefrom as an active ingredient, wherein the cosmetic composition inhibits an activity of tyrosinase and inhibits a production of melanin, resulting in an excellent skin whitening effect.

Also, the present invention provides a skin whitening method comprising a step of applying a cosmetic composition comprising a *Caragana Sinica* root extract, a fraction thereof or α-viniferin isolated therefrom as an active ingredient to skin.

A term "applying," used herein, means all the methods for putting the composition of the present invention in contact with an individual's skin in any appropriate manner, through which the present invention aims to let such composition absorbed into the skin.

The extract may be obtained by extracting a *Caragana Sinica* root with $C_1$ to $C_4$ lower alcohols or a mixed solvent thereof, wherein these lower alcohols may be ethanol or methanol, more specifically ethanol.

The extract, fraction or α-viniferin may be contained in 0.001 wt % to 30 wt % based on the total weight of a composition, more specifically contained in 0.01 wt % to 10 wt %.

The fraction of *Caragana Sinica* root extract may be obtained by adding an organic solvent selected from the group consisting of hexane, chloroform, ethyl acetate and butanol, more specifically by adding ethyl acetate, but is not limited thereto.

The afraction of *Caragana Sinica* root extract may contain 0.001 wt % to 30 wt % of α-viniferin based on the total weight of the fraction, more specifically may contain 0.01 wt % to 10 wt %, and even more specifically may contain 0.1 wt % to 1 wt %.

Also, the present invention provides a pharmaceutical composition for preventing or treating a melanin hyperpigmentation disease, comprising a *Caragana Sinica* root extract, a fraction thereof or α-viniferin isolated therefrom as an active ingredient.

A term "melanin hyperpigmentation," used in the present specification, means that a certain region of skin or nail becomes swarthier or darker compared to other regions due to an excessive increase in melanin.

The above melanin hyperpigmentation disease includes melasma, freckle, lentigo senilis, solar lentigines or the like, but is not limited thereto.

The above extract may be obtained by extracting a *Caragana Sinica* root with water, $C_1$ to $C_4$ lower alcohols or a mixed solvent thereof, wherein these lower alcohols may be ethanol or methanol, more specifically ethanol.

The extract, fraction or α-viniferin may be contained in 0.001 wt % to 30 wt % based on the total weight of a composition, more specifically 0.01 to 10 wt %.

The fraction of *Caragana Sinica* root extract may be obtained by adding an organic solvent selected from the group consisting of hexane, chloroform, ethyl acetate and butanol, more specifically by adding ethyl acetate, but is not limited thereto.

The fraction of *Caragana Sinica* root extract may contain 0.001 wt % to 30 wt % of α-viniferin based on the total weight of the fraction, more specifically may contain 0.01 wt % to 10 wt %, and even more specifically may contain 0.1 wt % to 1 wt %.

A pharmaceutical composition of the present invention may contain a pharmaceutically acceptable carrier in addition to an active ingredient, wherein this carrier is one conventionally used in preparation, including lactose, dextrose, sucrose, sorbitol, mannitol, starch, acacia rubber, calcium phosphate, alginate, gelatin, calcium silicate, microcrystalline cellulose, polyvinyl pyrrolidone, cellulose, water, syrup, methyl cellulose, methyl hydroxybenzoate, propyl hydroxybenzoate, talc, magnesium stearate, mineral oil and the like, but is not limited thereto. The pharmaceutical composition of the present invention may further contain lubricant, humectant, sweetening agent, flavoring agent, emulsifier, suspending agent, preservative, etc., in addition to the above ingredients. Suitable, pharmaceutically acceptable carriers and formulations are described in detail in Remington's Pharmaceutical Sciences (19th ed., 1995).

An appropriate dosage of the pharmaceutical composition of the present invention may be variously prescribed according to factors such as a formulation method, an administration method, a patient's age, weight, gender and pathological condition, food, administration time, administration route, excretion speed and reaction sensitivity. Meanwhile, the dosage of the pharmaceutical composition of the present invention may be preferably 0.0001-100 mg/kg (weight) per day.

The pharmaceutical composition of the present invention may be orally or parenterally administered, wherein in case of the parenteral administration, this may be administered through a local application to skin, an intravenous injection, a subcutaneous injection, an intramuscular injection, an intraperitoneal injection, a dermal administration, etc. Considering that the pharmaceutical composition of the present invention is applied for preventing or treating a melanin hyperpigmentation disease, it is preferable that the pharmaceutical composition is locally applied to skin.

A concentration of an active ingredient contained in the pharmaceutical composition of the present invention may be determined considering a treatment purpose, a patient's condition, a period required, etc., and is not limited to a certain range of concentration.

The pharmaceutical composition of the present invention may be prepared in a unit dose form or may be prepared by the pharmaceutical composition is inserted into a multidose container, in such a way that the pharmaceutical composition is formulated by means of a pharmaceutically acceptable carrier and/or excipient, according to a method, which may be easily carried out by those skilled in the art, to which the present invention pertains. At that time, a formulation may be solution, suspension or emulsion form in an oil or aqueous medium, or may be extract, powder, granule, tablet or capsule form, and may further contain a dispersing agent or a stabilizer.

In one embodiment of the present invention, a pharmaceutical composition of the present invention has a formulation for external use on skin. The formulation for external use on skin may be a powder, gel, ointment, cream, lotion, liquid or aerosol formulation, but is not limited thereto.

Advantageous Effects

The *Caragana Sinica* root extract, fraction thereof or α-viniferin isolated therefrom of the present invention inhibits an activity of tyrosinase and inhibits a production of melanin, resulting in having a skin whitening effect. Thus, the present invention may be valuably used as a cosmetic composition for whitening or a pharmaceutical composition for preventing or treating a melanin hyperpigmentation disease.

MODE FOR INVENTION

Hereinafter, the present invention will be described in detail through examples, experimental examples and formulation examples.

However, the following examples, experimental examples and formulation examples are set forth just as the illustrative description of the present invention, but are not to be construed to limit the content of the present invention.

Example 1: Preparing of a *Caragana Sinica* Root Extract 500 g of *Caragana Sinica* root, which was finely cut and dried in the shade, was pulverized to prepare a pulverized *Caragana Sinica* root. 5 l of 70% ethanol was added to the pulverized one, after which an extract was obtained by being reflux extracted for 5 hours and macerated. The extract was filtered with a 400-mesh filtering cloth, followed by filtered again with a filtering paper No. 2 (Whatman). After that, a final resulting filtrate was concentrated under reduced pressure to obtain 24 g of ethanol extract of *Caragana Sinica* root.

Examples 2 to 5: Preparing of a Fraction of *Caragana Sinica* Root Extract 10 g of the ethanol extract of *Caragana Sinica* root obtained from the Example 1 was solvent fractionated by means of a conventional method using hexane, chloroform, ethyl acetate and butanol, followed by concentrated under reduced pressure, such that 2.12 g of an hexane fraction of Example 2, 1.32 g of a chloroform fraction of Example 3, 1.24 g of an ethyl acetate fraction of Example 4 and 0.82 g of a butanol fraction of Example 5 were obtained, respectively.

Experimental Example 1: Isolation and Analysis of the Active Ingredient of the Fraction of *Caragana Sinica* Root Extract 0.1 g of each fraction of *Caragana Sinica* root extract obtained from the Examples 2 to 5 was dissolved in methanol to obtain 10 ml of test liquid. Also, 10 mg of a standard α-viniferin (C42H30O9:678.68) was dissolved in methanol so as to obtain a 100 ml solution, out of which 0.5 ml was dissolved again in methanol so as to obtain a 100 ml solution, and then this solution was diluted to 1/2 and 1/4 solutions to obtain standard solution. 20 μl of each of the test liquid and the standard solution was analyzed through an HPLC to measure a content of α-viniferin.

Figure 1:
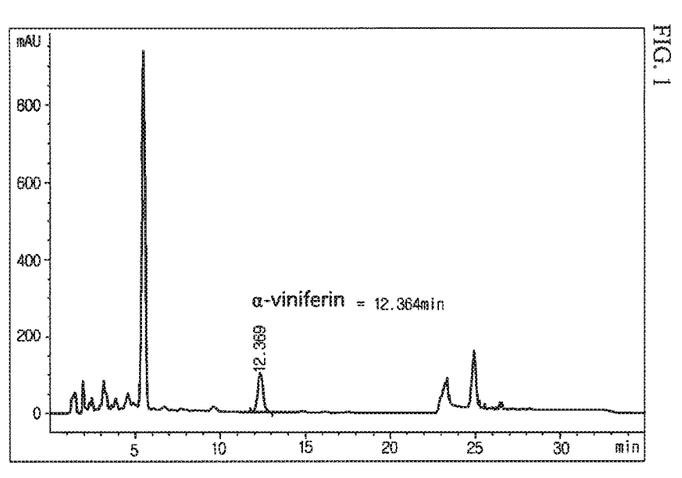
FIG. 1 shows results of analyzing an ingredient of an ethyl acetate fraction of an ethanol extract of *Caragana Sinica* root through a high-performance liquid chromatography (HPLC).
Figure 2:
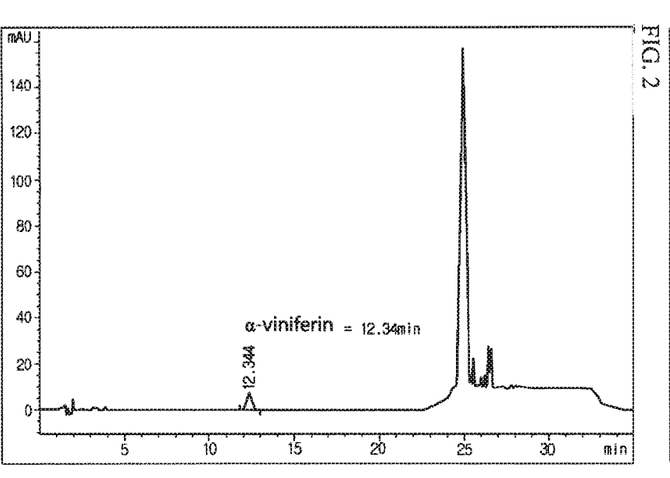
FIG. 2 shows results of analyzing an ingredient of α-viniferin isolated from the ethanol extract of *Caragana Sinica* root through the HPLC.

This HPLC analysis was made by means of Gilson HPLC System (Gilson Inc., Middleton, Wis., USA) equipped with an UV/VIS 151 detector. A 5 μm Hector-M C18 column (4.6 mm×250 mm; RS tech co., Daejeon, Korea) was used for a fixed phase. A mixed solution of 0.5% formic acid (A) and acetonitrile (B) was used for a mobile phase, wherein a content of B was increased from 30% to 100% with a certain gradient for 50 minutes. A flow rate was 0.8 ml per minute, and a detection wavelength of an UV detector was set to 280 nm. Results of HPLC analysis were shown in FIGS. 1 and 2. As a result, contents of α-viniferin of the Examples 2 to 5 were indicated in the following Table 1.

TABLE 1

| Sample | Content of α-viniferin (wt %) |
|---|---|
| Example 2 | — |
| Example 3 | 0.12% |
| Example 4 | 0.52% |
| Example 5 | 0.17% |

Also, the α-viniferin comprised in the ethyl acetate fraction of the ethanol extract of *Caragana Sinica* root obtained from the above Example 4 was identified through an NMR analysis.

Specifically, 15 g of the ethyl acetate fraction of the ethanol extract of *Caragana Sinica* root obtained from the above Example 4 was divided into 8 fractions (CE1 to CE8) by carrying out a silica gel column chromatography (2.5×28 an, EtOAc:MeOH=10:1→100% MeOH). With regard to a fraction CE7, the silica gel column chromatography (2.5×28 cm, CH2Cl2: MeOH=50:1→100% MeOH) and a sephadex LH-20 column chromatography (70% MeOH 100% MeOH) were performed to isolate 0.1 g of α-viniferin from the fraction.

Figure 3A:
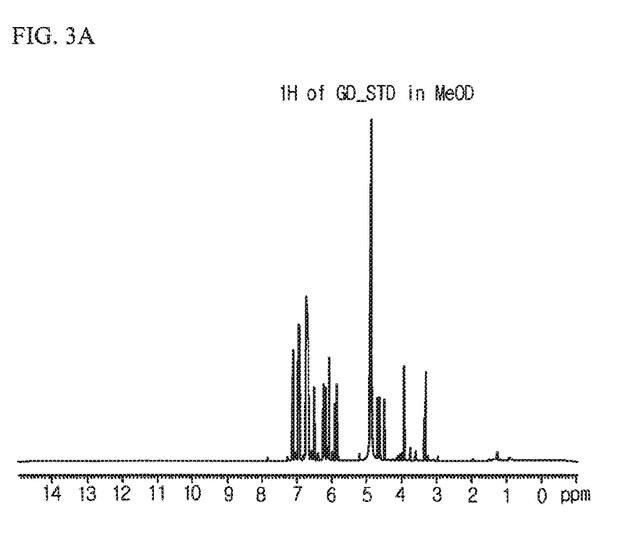
FIG. 3a shows results of analyzing the α-viniferin isolated from the ethyl acetate fraction of the ethanol extract of *Caragana Sinica* root through the 1H-nuclear magnetic resonance (1H-NMR).
Figure 3B:
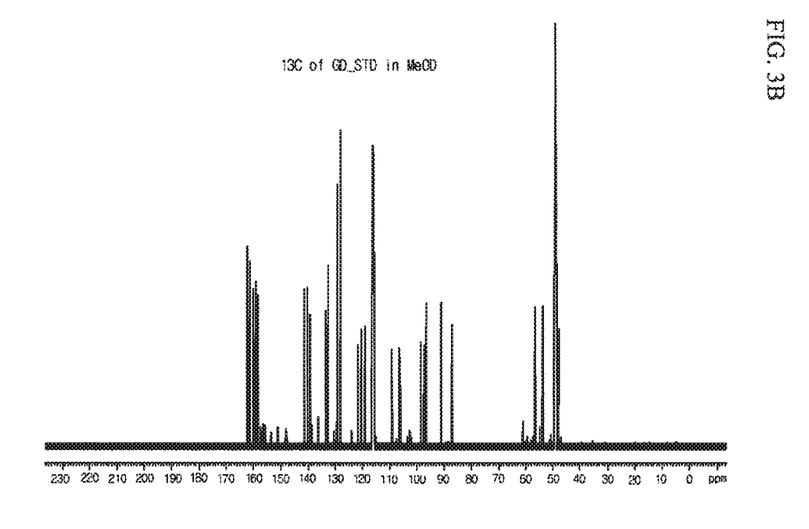
FIG. 3b shows results of analyzing the α-viniferin isolated from the ethyl acetate fraction of the ethanol extract of *Caragana Sinica* root through the 13C-NMR.

For NMR device, 1H-NMR of Varian (GEMINI, 500 MHz) and a 13C-NMR of Varian (GEMINI, 200 MHz) were used to analyze a structure of the α-viniferin, wherein a solvent used therefor was acetone-d6, purchased from Aldrich, and an internal standard substance used therefor was trimethylsilane so as to indicate results as a δ value (ppm), wherein NMR results were shown in FIGS. 3a and 3b.

1H-NMR (500 MHz, Acetone-d): δppm 4.11 (s, 1H, H-3(I)), 4.77 (d, 1H, H-3(II)), 4.85 (d, 1H, H-3(II)), 5.05 (d, 1H, H-2(III)), 6.09 (d, 1H, H-2(II)), 6.14 (d, 1H, H-5(I)), 6.22 (s, 1H, H-2(I)), 6.38 (m, 3H, H-7(I, II, III)), 6.74 (d, 1H, H-5(III)), 6.87 (m, 3H, H-3', 5'(I), H-5(II)), 6.92 (m, 4H, H-3', 5'(II, III)), 7.18 (m, 4H, H-2', 6'(I, III)), 7.36 (m, 2H, H-2', 6' (II))

13C-NMR (125 MHz, Acetone-d): δppm 46.4 (C-3(I)), 52.8 (C-3(II)), 55.7 (C-3(III)), 86.4 (C-2(I)), 90.0 (C-2(II)), 95.6 (C-2(III)), 96.6 (C-7(II, III)), 98.0 (C-7(I)), 105.8 (C-5(III)), 106.2 (C-5(II)), 108.5 (C-5(I)), 115.7 (C-3', 5' (I)), 116.1 (C-3', 5' (III,II)), 118.8 (C-3a(I)), 119.7 (C-3a (III)), 120.9 (C-3a(II)), 128.1 (C-2', 6' (I)), 128.2 (C-2', 6' (II)), 128.6 (C-2', 6' (III)), 132.0 (C-1' (I)), 132.3 (C-1' (II)), 132.5 (C-1' (III)), 138.7 (C-4(III)), 159.4 (C-6(II,I)), 160.7 (C-7a(II)), 160.8 (C-6(III)), 161.6 (C-7a(I)), 161.8 C-7a (III))

Experimental Example 2: Confirming Whitening Effect of the *Caragana Sinica* Root Extract and the Fraction Thereof Experimental Example 2-1: Confirming Tyrosinase Activity Inhibitory Effect of the *Caragana Sinica* Root Extract and the Fraction Thereof A tyrosinase is an enzyme that promotes an oxidization process of a substance called tyrosine in vivo to produce a melanin. Thus, it was confirmed that the ethanol extract of *Caragana Sinica* root and the fraction thereof prepared from the above Examples 1 to 5 had an inhibitory effect on an activity of tyrosinase.

Specifically, tyrosinase, isolated and refined from a mushroom, was bought from Sigma L-tyrosine, as a substrate, was dissolved in 0.05 M sodium phosphate buffer solution (pH 6.8) to obtain a 0.1 mg/ml solution, after which the ethanol extract of *Caragana Sinica* root and the fraction thereof obtained from the above Examples 1 to 5 were dissolved in 0.05 M sodium phosphate buffer solution (pH 6.8) at a concentration of 0.05%, 0.1% and 0.2%. After that, 0.5 ml of a resulting L-tyrosine solution was inserted into a test tube, after which 0.5 ml of a sample fluid of the above *Caragana Sinica* root extract and the fraction thereof was added thereto, such that the test tube of a resulting mixture was left alone in a 37° C. constant temperature chamber for 10 minutes. After that, 0.5 ml of 200 unit/ml tyrosinase was added, followed by reacted at 37° C. for 10 minutes. The reaction was stopped by placing the test tube containing that reaction solution on ice to be rapidly cooled down, after which an absorbance of the resulting product was measured with a spectrophotometer at a wavelength of 475 nm. Control group was one containing 0.5 ml of a buffer solution instead of the *Caragana Sinica* root extract, and the comparison target was arbutin, well-known as a skin whitening agent. At that time, an inhibition rate of tyrosinase activity (%) was calculated according to the following Mathematical formula 1, wherein results thereof were shown in the following Table 2.

[Mathematical formula 1]

$$\text{Inhibition rate of tyrosinase activity (\%)} = 100 - \left[\frac{\text{Absorbance of test group}}{\text{Absorbance of control group}}\right] \times 100$$

TABLE 2

| Sample | Concentration | Inhibition rate of tyrosinase activity (%) |
|---|---|---|
| Example 1 | 0.2% | 67.2 |
|  | 0.1% | 45.8 |
|  | 0.05% | 32.2 |
| Example 2 | 0.2% | 45.5 |
|  | 0.1% | 23.2 |
|  | 0.05% | 13.2 |
| Example 3 | 0.2% | 53.1 |
|  | 0.1% | 31.2 |
|  | 0.05% | 16.4 |

TABLE 2-continued

| Sample | Concentration | Inhibition rate of tyrosinase activity (%) |
|---|---|---|
| Example 4 | 0.2% | 79.2 |
|  | 0.1% | 55.8 |
|  | 0.05% | 36.2 |
| Example 5 | 0.2% | 49.7 |
|  | 0.1% | 29.2 |
|  | 0.05% | 12.4 |
| Arbutin | 0.2% | 78.7 |
|  | 0.1% | 38.4 |
|  | 0.05% | 21.2 |

As a result, as shown in the Table 2, the *Caragana Sinica* root extract and the fraction thereof obtained from the Examples 1 to 5 inhibited an activity of tyrosinase in a concentration-dependent manner. In particular, when the ethyl acetate fraction of *Caragana Sinica* root extract of the Example 4 was compared with arbutin as a positive control group, the former showed an inhibitory effect similar to the latter one. Thus, it was confirmed that the ethyl acetate fraction of *Caragana Sinica* root extract had an excellent effect on inhibiting an activity of tyrosinase.

Experimental Example 2-2: Confirming Melanin Production Inhibitory Effect of the *Caragana Sinica* Root Extract and the Fraction Thereof In order to confirm a whitening effect of the ethanol extract of *Caragana Sinica* root and the fraction thereof prepared in the above Examples 1 to 5, its effect on inhibiting a production of melanin was confirmed with regard to a B16F1 melanin-forming cell.

Specifically, the B16F1 melanin-forming cells, as a mouse-derived cell line, were obtained from American Type Culture Collection (ATCC) to use. The B16F1 melanin-forming cells were divided into a 6-well plate at a concentration of $2 \times 10^5$ per well, after which the cells were attached thereto, thus being divided at such a concentration as not to cause toxicity. After that, the ethanol extract of *Caragana Sinica* root and the fraction thereof obtained from the above Examples 1 to 5 were treated at each concentration, and then being cultured for 72 hours. After this 72-hour cultivation, the cells were taken off by trypsin-EDTA, after which the number of cells was measured, and then cells were collected by centrifugation. A quantification of melanin in cells was performed in such a way that modifying method of Lotan (Cancer Res., 40: 3345-3350, 1980). A cell pallet was washed once with PBS, after which 1 ml of a homogenization buffer solution (50 mM sodium phosphate, pH6.8, 1% Triton X-100, 2 mM PMSF) was added thereto and swirled for 5 minutes to crush the cells. 1N NaOH (10% DMSO) was added to a cell lysate obtained through centrifugation (3,000 rpm, 10 minutes) so as to dissolve the extracted melanin, after which an absorbance of the melanin was measured by microplate reader at 405 nm, and the melanin was quantified to measure an inhibition rate of melanin production (%) of a sample. The inhibition rate of melanin production (%) of the B16F1 melanin-forming cell was calculated according to the following [Mathematical formula 2], wherein results thereof were indicated at Table 3.

[Mathematical formula 2]

$$\text{Inhibition rate of melanin production (\%)} = \left[\frac{A-B}{A}\right] \times 100$$

A: Amount of melanin in a well without a sample added

B: Amount of melanin in a well with a sample added

TABLE 3

| Sample | Treatment concentration (μg/ml) | Inhibition rate of melanin production (%) |
|---|---|---|
| Untreated group | 0.2 | — |
| Example 1 | 200 | 75.3 |
|  | 100 | 60.5 |
| Example 2 | 200 | 69.4 |
|  | 100 | 51.9 |
| Example 3 | 200 | 71.7 |
|  | 100 | 58.9 |
| Example 4 | 200 | 82.1 |
|  | 100 | 69.6 |
| Example 5 | 200 | 34.7 |
|  | 100 | 24.9 |
| Arbutin | 200 | 75.7 |
|  | 100 | 63.5 |

As a result, as shown in the Table 3, it was confirmed that the *Caragana Sinica* root extract and the fraction thereof obtained from the Examples 1 to 5 inhibited a production of melanin in a concentration-dependent manner. In particular, it was confirmed that the ethyl acetate fraction of the *Caragana Sinica* root extract of the Example 4 showed more excellent inhibitory effect on the production of melanin than arbutin known as a whitening agent.

Experimental Example 2-3: Confirming Inhibitory Effect of α-Viniferin on Melanin Production In order to confirm whitening effect of α-viniferin isolated from the fraction of *Caragana Sinica* root of the above Example 4, its effect on inhibiting a production of melanin was confirmed with regard to a B16F1 melanin-forming cell.

Specifically, the α-viniferin isolated from the ethyl acetate fraction of the ethanol extract of *Caragana Sinica* root obtained from the above Example 4 or arbutin, and α-MSH, a stimulant of melanin production, were treated at the same time, after which an amount of melanin was measured in 70 to 74 hours later as describe in the above Example 2-2.

Figure 4:
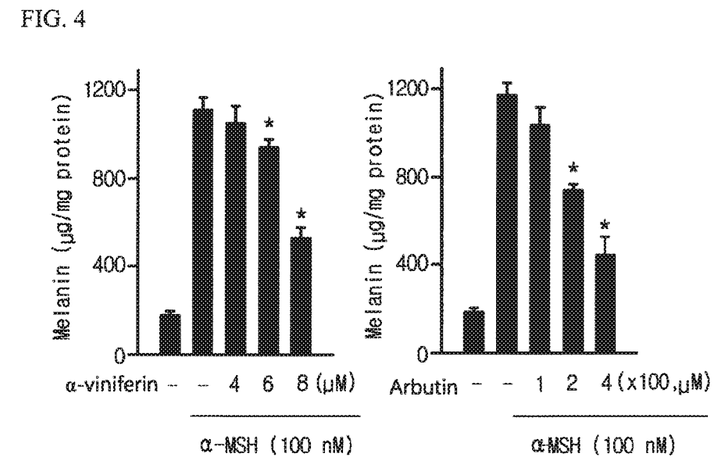
FIG. 4 shows a melanin production inhibitory effect of the α-viniferin isolated from the ethyl acetate fraction of the ethanol extract of *Caragana Sinica* root.

As a result, as shown in FIG. 4, an inhibitory effect of α-viniferin on melanin production, which was induced by α-MSH, was indicated as inhibition rate of 8% at a sample concentration of 4 μM, 21% at 6 μM and 63% at 8 μM respectively, and an IC50 value was 7 μM. On the other hand, in case of arbutin, a control substance, its inhibitory effect on melanin production, which was induced by α-MSH stimulation, was indicated as inhibitory rate of 13% at a sample concentration of 100 μM, 44% at 200 μM and 73% at 400 μM respectively, and an IC50 value was 242 μM. Thus, it was confirmed that a whitening effect of α-viniferin on melanin production, which was induced by α-MSH, was about 35 times higher than that of arbutin.

Formulation Example 1: Preparing of a Solubilized Formulation Comprising the Fraction of *Caragana Sinica* Root Extract In order to confirm a stability of a cosmetic composition comprising a fraction of *Caragana Sinica* root extract as an active ingredient, the ethyl acetate fraction of *Caragana Sinica* root extract of the above Example 4 was dissolved in the mixed solvent of buthylene glycol and purified water at a ratio of 50:50, and then a solubilized formulation was prepared such as that shown in the following Table 4.

TABLE 4

| Phase | Ingredient | Content (%) |
| --- | --- | --- |
| Water phase | Purified water | To 100 |
| | Glycerin | 10-25 |
| | Dipropylene Glycol | |
| | Betaine | |
| | D-panthenol | |
| | Sodium Hyaluronate | |
| | Thickener | Suitable amount |
| | Metal ion sequestering agent | Suitable amount |
| Solubilized phase | PEG-60 hydrogenated castor oil | 0-2 |
| | PEG-40 hydrogenated castor oil | 0-2 |
| | Polyhydric alcohol | 0-10 |
| | Fragrance | Suitable amount |
| | Ethanol | 0-20 |
| Addition I | Ethyl acetate fraction of *Caragana Sinica* root extract of Example 4 | 3.2 |
| Addition II | Preservative | Suitable amount |
| | Other additive | Suitable amount |

Preparation Method (1) Water phase and solubilized phase were evenly mixed and dissolved, respectively.

(2) The solubilized phase was inserted into the water phase to be mixed and solubilized together.

(3) An addition I, comprising the ethyl acetate fraction of *Caragana Sinica* root extract of the Example 4, was solubilized and inserted into the resulting solution to be mixed together, after which an addition II was mixed into the resulting mixture to complete a solubilized formulation.

Formulation Example 2: Preparing of an Essence Formulation Comprising the Fraction of *Caragana Sinica* Root Extract In order to confirm a stability of the cosmetic composition comprising a fraction of *Caragana Sinica* root extract as an active ingredient, the ethyl acetate fraction of *Caragana Sinica* root extract of the above Example 4 was dissolved in the mixed solvent of buthylene glycol and purified water at a ratio of 50:50, and then an essence formulation was prepared such as that shown in the following Table 5.

TABLE 5

| Phase | Ingredient | Content (%) |
| --- | --- | --- |
| Water phase | Purified water | To 100 |
| | Ceteareth-6 olivate | 0.1-3 |
| | Glycerin | 10-25 |
| | 1,2-propanediol | |
| | Sodium Hyaluronate | |
| | Thickener | Suitable amount |
| | Metal ion sequestering agent | Suitable amount |
| Oil phase | PEG-100 Stearate | 0.1-1 |
| | Glyceryl Stearate | 0.1-1 |
| | Polysorbate 60 | 0.1-1 |
| | Cetyl alcohol | 0.1-1 |
| | Behenyl alcohol | 0.1-1 |
| | Squalane | 5-20 |
| | Tocopheryl Acetate | 0.1-0.5 |
| | Ethyl acetate fraction of *Caragana Sinica* root extract of Example 4 | 3.2 |

TABLE 5-continued

| Phase | Ingredient | Content (%) |
| --- | --- | --- |
| Additional phase I | Fragrance | Suitable amount |
| Additional phase II | Preservative | Suitable amount |
| | Other additive | Suitable amount |

Preparation Method (1) Water phase and oil phase were heated to be evenly mixed and dissolved, respectively.

(2) The oil phase was inserted into the water phase at 75° C. to be mixed and emulsified together.

(3) An additional phase I, comprising the ethyl acetate fraction of *Caragana Sinica* root extract of the Example 4 as an active ingredient, was inserted into the resulting solution at 50° C. to be mixed together, after which an additional phase II was mixed into the resulting mixture.

Formulation Example 3: Preparing of a Cream Formulation Comprising the Fraction of *Caragana Sinica* Root Extract In order to confirm a stability of the cosmetic composition comprising a fraction of *Caragana Sinica* root extract as an active ingredient, the ethyl acetate fraction of *Caragana Sinica* root extract of the above Example 4 was dissolved in the mixed solvent of buthylene glycol and purified water at a ratio of 50:50, and then a cream formulation was prepared such as that shown in the following Table 6.

TABLE 6

| Phase | Ingredient | Content (%) |
| --- | --- | --- |
| Water phase | Purified water | To 100 |
| | Glycerin | 10-25 |
| | Betaine | |
| | Sodium Hyaluronate | |
| | Thickener | Suitable amount |
| | Metal ion sequestering agent | Suitable amount |
| Oil phase | PEG-100 Stearate | 0.1-2 |
| | Glyceryl Stearate | 0.1-2 |
| | Polysorbate 60 | 0.1-2 |
| | Stearic Acid | 0.1-2 |
| | Cetearyl Alcohol | 0.1-2 |
| | Capric/Caprylic Triglyceride | 10-30 |
| | Tocopheryl Acetate | 0.1-0.5 |
| Addition I | Ethyl acetate fraction of *Caragana Sinica* root extract of Example 4 | 3.2 |
| Addition II | Fragrance | Suitable amount |
| | Preservative | Suitable amount |
| | Other additive | Suitable amount |

Preparation Method (1) Water phase and oil phase were heated to evenly mixed and dissolved, respectively.

(2) The oil phase was inserted into the water phase at 75° C. to be mixed and emulsified together.

(3) An additional phase I, comprising the ethyl acetate fraction of *Caragana Sinica* root extract of the Example 4 as an active ingredient, was inserted into the resulting solution at 50° C. to be mixed together, after which an additional phase II was mixed into the resulting mixture.

Experimental Example 3: Confirming a Stability of the Cosmetic Composition Comprising a Fraction of *Caragana Sinica* Root Extract

Experimental Example 3-1: Confirming a Raw Material Stability of the Cosmetic Composition Comprising the Fraction of *Caragana Sinica* Root Extract In order to confirm a raw material stability, the solubilized formulation, essence formulation and cream formulation of the above Formulation Examples 1 to 3 were stored under a condition of 4° C., 30° C., 45° C. and sunlight for 12 weeks, and then changes of α-viniferin ingredient comprised in the ethyl acetate fraction of *Caragana Sinica* root extract with the passage of time were observed through an HPLC analysis by the same method of the above Experimental Example 1, wherein results thereof were shown in the following Table 7.

TABLE 7

| | α-viniferin (compared to the initial content %) | | | | | | | | | | | |
|---|---|---|---|---|---|---|---|---|---|---|---|---|
| | Solubilized formulation | | | | Essence formulation | | | | Cream formulation | | | |
| Elapsed time | 4° C. | 30° C. | 45° C. | Sunlight | 4° C. | 30° C. | 45° C. | Sunlight | 4° C. | 30° C. | 45° C. | Sunlight |
| Initial | 99.9 | 100 | 99 | 99.2 | 99 | 99.8 | 100 | 99.3 | 100 | 99.5 | 99.3 | 100 |
| 1 week | 96.2 | 96.7 | 97.2 | 97 | 97.3 | 96.6 | 96 | 97.7 | 97 | 96.2 | 95.7 | 94.4 |
| 3 week | 97 | 97.6 | 97.3 | 94.3 | 97 | 98.1 | 98.5 | 97.1 | 96.7 | 97.7 | 98.3 | 92.4 |
| 5 week | 97.6 | 98.2 | 97.7 | 90.9 | 96.1 | 96.1 | 98.8 | 96.3 | 95.8 | 96.8 | 99.4 | 92 |
| 8 week | 96.6 | 99 | 94.6 | 86.4 | 94.3 | 96 | 96.6 | 96.9 | 96.4 | 95.2 | 100.2 | 90.9 |
| 12 week | 94.9 | 94.2 | 98.7 | 92.3 | 97 | 95.7 | 98.1 | 94.2 | 95.9 | 93.9 | 101.7 | 88.9 |
| Result | Stable | Stable | Stable | Stable | Stable | Stable | Stable | Stable | Stable | Stable | Stable | Stable |

As a result, as shown in the Table 7, it was confirmed that the solubilized formulation, essence formulation and cream formulation all showed an excellent stability of α-viniferin, an active ingredient inside the ethyl acetate fraction of *Caragana Sinica* root extract, under a high temperature condition and a sunlight condition.

Experimental Example 3-2: Confirming a Formulation Stability of the Cosmetic Composition Comprising a Fraction of *Caragana Sinica* Root Extract In order to confirm a formulation stability, the solubilized formulation, essence formulation and cream formulation of the above Formulation Examples 1 to 3 were stored under a condition of 4° C., 30° C., 45° C. and sunlight for 12 weeks, after which changes in color, odor and formulation thereof were observed through a visual evaluation and a sensory evaluation, wherein results thereof were shown in the following Tables 8 to 10. For this, a degree of color, odor and formulation changes was classified and evaluated according to following evaluation criteria.

<Evaluation Criteria>
No change: ○
Slight change: Δ
Significant change: x

TABLE 8

| | Solubilized formulation | | | | | | | | | | | |
|---|---|---|---|---|---|---|---|---|---|---|---|---|
| | Change in odor | | | | Change in color | | | | Change in formulation | | | |
| Elapsed time | 4° C. | 30° C. | 45° C. | Sunlight | 4° C. | 30° C. | 45° C. | Sunlight | 4° C. | 30° C. | 45° C. | Sunlight |
| 1 week | ○ | ○ | ○ | ○ | ○ | ○ | ○ | ○ | ○ | ○ | ○ | ○ |
| 2 week | ○ | ○ | ○ | ○ | ○ | ○ | ○ | ○ | ○ | ○ | ○ | ○ |
| 4 week | ○ | ○ | ○ | ○ | ○ | ○ | ○ | ○ | ○ | ○ | ○ | ○ |
| 8 week | ○ | ○ | ○ | ○ | ○ | ○ | ○ | ○ | ○ | ○ | ○ | ○ |
| 12 week | ○ | ○ | ○ | ○ | ○ | ○ | ○ | ○ | ○ | ○ | ○ | ○ |

TABLE 9

| | Essence formulation | | | | | | | | | | | |
|---|---|---|---|---|---|---|---|---|---|---|---|---|
| | Change in odor | | | | Change in color | | | | Change in formulation | | | |
| Elapsed time | 4° C. | 30° C. | 45° C. | Sunlight | 4° C. | 30° C. | 45° C. | Sunlight | 4° C. | 30° C. | 45° C. | Sunlight |
| 1 week | ○ | ○ | ○ | ○ | ○ | ○ | ○ | ○ | ○ | ○ | ○ | ○ |
| 2 week | ○ | ○ | ○ | ○ | ○ | ○ | ○ | ○ | ○ | ○ | ○ | ○ |
| 4 week | ○ | ○ | ○ | ○ | ○ | ○ | ○ | ○ | ○ | ○ | ○ | ○ |
| 8 week | ○ | ○ | ○ | ○ | ○ | ○ | ○ | ○ | ○ | ○ | ○ | ○ |
| 12 week | ○ | ○ | ○ | ○ | ○ | ○ | ○ | ○ | ○ | ○ | ○ | ○ |

TABLE 10

| | Cream formulation | | | | | | | | | | | |
|---|---|---|---|---|---|---|---|---|---|---|---|---|
| | Change in odor | | | | Change in color | | | | Change in formulation | | | |
| Elapsed time | 4° C. | 30° C. | 45° C. | Sunlight | 4° C. | 30° C. | 45° C. | Sunlight | 4° C. | 30° C. | 45°c | Sunlight |
| 1 week | ○ | ○ | ○ | ○ | ○ | ○ | ○ | ○ | ○ | ○ | ○ | ○ |
| 2 week | ○ | ○ | ○ | ○ | ○ | ○ | ○ | ○ | ○ | ○ | ○ | ○ |
| 4 week | ○ | ○ | ○ | ○ | ○ | ○ | ○ | ○ | ○ | ○ | ○ | ○ |
| 8 week | ○ | ○ | ○ | ○ | ○ | ○ | ○ | ○ | ○ | ○ | ○ | ○ |
| 12 week | ○ | ○ | ○ | ○ | ○ | ○ | ○ | ○ | ○ | ○ | ○ | ○ |

As a result, as shown in the Tables 8 to 10, it was confirmed that the solubilized formulation, essence formulation and cream formulation all showed an excellent stability under a high temperature condition and a sunlight condition.

Experimental Example 3-3: Confirming a Stability of α-Viniferin Isolated from the Fraction of Caragana Sinica Root Extract In order to confirm a stability of α-viniferin, the α-viniferin isolated from the ethyl acetate fraction of the ethanol extract of Caragana Sinica root obtained from the above Experimental Example 1 was stored under a condition of 50° C. for 2 weeks, after which content changes thereof were observed through an HPLC analysis by the same method of the above Experimental Example 1. A control group was kobophenol A isolated from the Caragana Sinica root extract, which was stored under the same condition with that of the α-viniferin, after which content changes thereof were observed by the same method. Results thereof were shown in the following Table 11.

TABLE 11

| Test Condition and Period | Kobophenol A | α-viniferin |
|---|---|---|
| Initial | 121.4 ppm | 252.8 ppm |
| 1 week | 115.6 ppm | 249.60 ppm |
| | 95.2% | 98.7% |
| 2 weeks | 103.6 ppm | 253.45 ppm |
| | 85.3% | 100.3% |

As a result, as shown in the Table 11, a content of the α-viniferin was not decreased at a high temperature of 50° C. for 2 weeks, and thus it was confirmed that the α-viniferin had an excellent stability compared to kobophenol A, i.e. another whitening substance of Caragana Sinica root extract.

Experimental Example 4: Confirming Skin Irritation of the Cosmetic Composition Comprising the Fraction of Caragana Sinica Root Extract In order to confirm a skin irritation of the cosmetic composition comprising the fraction of Caragana Sinica root extract, evaluation on the skin irritation of a cream formulation of the above Formulation Example 3 was conducted.

Specifically, a 5×20 cm patch with a certain amount (20 µl) of the cream formulations, comprising the ethyl acetate fraction of the ethanol extract of Caragana Sinica root prepared from the above Formulation Example 3 in a concentration-dependent manner, were attached onto the back of 30 adults for 24 hours, after which the patch was removed therefrom and changes in skin conditions were read with naked eyes at 1 and 24 hours later, wherein the results were shown in the following Table 12. For this, a degree of changes in skin conditions was classified and evaluated according to following evaluation criteria for skin conditions.

<Evaluation Criteria for Skin Conditions>
0: No change
1: Extremely slight change
2: Slight change
3: Slightly severe change
4: Severe change
5: Extremely severe change

TABLE 12

| Subject (gender and skin type) | Elapsed Time | Skin Condition according to Fraction Content | | |
|---|---|---|---|---|
| | | 3.2% | 6.4% | 16% |
| 1 (M, Neutral) | 1 hour | 0 | 0 | 0 |
| | 24 hours | 0 | 0 | 0 |

TABLE 12-continued

| Subject (gender and skin type) | Elapsed Time | Skin Condition according to Fraction Content | | |
|---|---|---|---|---|
| | | 3.2% | 6.4% | 16% |
| 2 (F, Neutral) | 1 hour | 0 | 0 | 0 |
| | 24 hours | 0 | 0 | 0 |
| 3 (F, Neutral) | 1 hour | 0 | 0 | 0 |
| | 24 hours | 0 | 0 | 0 |
| 4 (F, Neutral) | 1 hour | 0 | 0 | 0 |
| | 24 hours | 0 | 0 | 0 |
| 5 (F, Neutral) | 1 hour | 0 | 0 | 0 |
| | 24 hours | 0 | 0 | 0 |
| 6 (F, Neutral) | 1 hour | 0 | 0 | 0 |
| | 24 hours | 0 | 0 | 0 |
| 7 (M, Neutral) | 1 hour | 0 | 0 | 0 |
| | 24 hours | 0 | 0 | 0 |
| 8 (F, Neutral) | 1 hour | 0 | 0 | 0 |
| | 24 hours | 0 | 0 | 0 |
| 9 (F, Neutral) | 1 hour | 0 | 0 | 0 |
| | 24 hours | 0 | 0 | 0 |
| 16 (F, Neutral) | 1 hour | 0 | 0 | 0 |
| | 24 hours | 0 | 0 | 0 |
| 11 (F, Neutral) | 1 hour | 0 | 0 | 0 |
| | 24 hours | 0 | 0 | 0 |
| 12 (F, Neutral) | 1 hour | 0 | 0 | 0 |
| | 24 hours | 0 | 0 | 0 |
| 13 (F, Neutral) | 1 hour | 0 | 0 | 0 |
| | 24 hours | 0 | 0 | 0 |
| 14 (F, Neutral) | 1 hour | 0 | 0 | 0 |
| | 24 hours | 0 | 0 | 0 |
| 15 (F, Neutral) | 1 hour | 0 | 0 | 0 |
| | 24 hours | 0 | 0 | 1 |
| 16 (F, Neutral) | 1 hour | 0 | 0 | 0 |
| | 24 hours | 0 | 0 | 0 |
| 17 (F, Neutral) | 1 hour | 0 | 0 | 0 |
| | 24 hours | 0 | 0 | 0 |
| 18 (F, Neutral) | 1 hour | 0 | 0 | 0 |
| | 24 hours | 0 | 0 | 0 |
| 19 (F, Neutral) | 1 hour | 0 | 0 | 0 |
| | 24 hours | 0 | 0 | 0 |
| 20 (F, Neutral) | 1 hour | 0 | 0 | 0 |
| | 24 hours | 0 | 0 | 0 |
| 21 (M, Neutral) | 1 hour | 0 | 0 | 0 |
| | 24 hours | 0 | 0 | 0 |
| 22 (F, Neutral) | 1 hour | 0 | 0 | 0 |
| | 24 hours | 0 | 0 | 0 |
| 23 (F, Neutral) | 1 hour | 0 | 0 | 0 |
| | 24 hours | 0 | 0 | 1 |
| 24 (F, Neutral) | 1 hour | 0 | 0 | 0 |
| | 24 hours | 0 | 0 | 0 |
| 25 (F, Neutral) | 1 hour | 0 | 0 | 0 |
| | 24 hours | 0 | 0 | 0 |
| 26 (F, Neutral) | 1 hour | 0 | 0 | 0 |
| | 24 hours | 0 | 0 | 0 |
| 27 (F, Neutral) | 1 hour | 0 | 0 | 0 |
| | 24 hours | 0 | 0 | 0 |
| 28 (F, Neutral) | 1 hour | 0 | 0 | 0 |
| | 24 hours | 0 | 0 | 0 |
| 29 (F, Neutral) | 1 hour | 0 | 0 | 0 |
| | 24 hours | 0 | 0 | 0 |
| 30 (F, Neutral) | 1 hour | 0 | 0 | 0 |
| | 24 hours | 0 | 0 | 1 |

As a result, as shown in the Table 12, it was identified that the cream formulation comprising high content of α-viniferin had a little skin irritation, too.

Experimental Example 5: Clinical Evaluation of Effectiveness of the Cosmetic Composition Comprising the Fraction of *Caragana Sinica* Root Extract In order to evaluate an effectiveness of the cosmetic composition comprising the fraction of *Caragana Sinica* root extract, a clinical test was conducted with 23 women with an average age of 44. A test product was a cosmetic composition comprising the fraction of *Caragana Sinica* root extract by 3.2%, and a control product was a placebo cream comprising purified water instead of the fraction of *Caragana Sinica* root extract of the test product. The test product and the control product were respectively applied onto left and right sides of a subject face at random, and were applied thereto again at an interval of twice a day, wherein the changes were observed for 8 weeks.

Experimental Example 5-1: Clinical Evaluation of Skin Brightness Changes According to Application of the Cosmetic Composition Comprising the Fraction of *Caragana Sinica* Root Extract In order to confirm a change in skin brightness according to a use of the test and control products, the skin brightness was measured before use and in 4, 6 and 8 weeks after use employing Chroma meter CM700d for a skin color measuring apparatus. In every measurement, skin brightness of the same region was measured three times, wherein an average value thereof was used as an evaluation material.

TABLE 13

| Classification | Test Product | | Control Product | | Significance Probability of Test-Control Comparison |
|---|---|---|---|---|---|
| | Brightness (L*) | Significance Probability | Brightness (L*) | Significance Probability | |
| Test of within-subject effect | — | 0.000* | — | 0.000* | — |
| Before use | 62.567 ± 3.117 | — | 63.114 ± 2.802 | — | — |
| 4 weeks after use | 65.235 ± 2.761 | 0.121 | 63.544 ± 2.265 | 0.696 | 0.554 |
| 6 weeks after use | 67.346 ± 2.912 | 0.045* | 62.239 ± 2.450 | 0.062 | 0.000** |
| 8 weeks after use | 68.565 ± 2.559 | 0.000* | 62.507 ± 2.215 | 0.306 | 0.000** |

Figure 5:
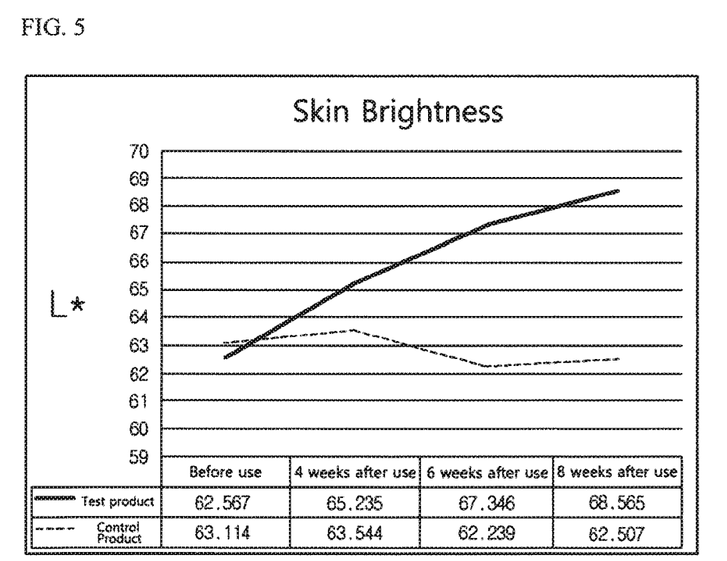
FIG. 5 shows results of a clinical evaluation on skin brightness changes according to an application of a cosmetic composition comprising a fraction of *Caragana Sinica* root extract.

*$p < 0.05$ Post-hoc test results of a non-parametric test, which was repeatedly measured by a parametric method ANOVA according to a test of normality
**$p < 0.05$ Independent sample t test result In the Table 13, data showed that the results of measuring a skin brightness of 23 subjects were indicated as an average±standard error (SE), wherein a degree of their changes was illustrated in graph in FIG. 5.

As seen in Table 13 and FIG. 5, measured value of skin brightness after use of the test product were significantly increased (significance probability <0.05) in 6 and 8 weeks after use in comparison with before use, and also showed a significant difference (significance probability <0.05) in 6 and 8 weeks after use in comparison with the control product. Accordingly, it was confirmed that the cosmetic composition comprising the fraction of *Caragana Sinica* root extract gave a benefit to the skin brightness from 6 weeks after use.

Experimental Example 5-2: Clinical Evaluation of Skin Melanin Content Changes According to Application of the Cosmetic Composition Comprising the Fraction of *Caragana Sinica* Root Extract In order to confirm a change in skin brightness according to the use of the test and control products, an amount of skin melanin was measured before use and in 4, 6 and 8 weeks after use by using a reflected light from a probe at 568 nm (green), 660 nm (red), 880 nm (infrared) employing a narrow-band reflectance spectrophotometer called Mexameter. In every measurement, an amount of melanin of the same region was measured three times, wherein an average value thereof was used as an evaluation material.

TABLE 14

Figure 6:
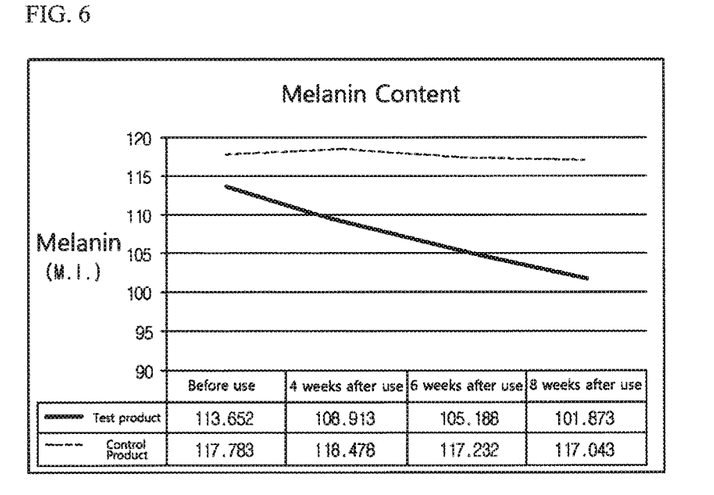
FIG. 6 shows results of a clinical evaluation on melanin content changes of skin according to the application of the cosmetic composition comprising the fraction of *Caragana Sinica* root extract.

| Classification | Test Product Brightness (L*) | Test Product Significance Probability | Control Product Brightness (L*) | Control Product Significance Probability | Significance Probability of Test-Control Comparison |
|---|---|---|---|---|---|
| Test of within-subject effect | — | 0.000* | — | 0.198 | — |
| Before use | 113.652 ± 30.693 | — | 117.783 ± 32.342 | — | — |
| 4 weeks after use | 108.913 ± 26.258 | 0.068 | 118.478 ± 27.860 | — | 0.008## |
| 6 weeks after use | 105.188 ± 26.619 | 0.000# | 117.232 ± 32.130 | — | 0.000# |
| 8 weeks after use | 101.873 ± 26.170 | 0.001# | 117.043 ± 32.472 | — | 0.003## | p < 0.017 (=5%/3) Results of conducting a Friedman test as a non-parametric method and then a post-hoc test with a non-parametric test method according to a test of normality
p < 0.05 Mann-Whitney U test results In the Table 14, data showed that the results of 23 subjects were indicated as an average±standard error (SE), wherein a degree of their changes was illustrated in graph in FIG. 6.

As seen in Table 14 and FIG. 6, measured value of skin melanin after use of the test product were significantly decreased (significance probability <0.017) in 6 and 8 weeks after use in comparison with before use, and also showed a significant difference (significance probability <0.05) in 4, 6 and 8 weeks after use in comparison with the control product. Accordingly, it was confirmed that the cosmetic composition comprising the fraction of *Caragana Sinica* root extract was beneficial to decrease a content of skin melanin from 6 weeks after use.

Experimental Example 5-3: Visual Evaluation of Skin Color Changes According to Application of the Cosmetic Composition Comprising the Fraction of *Caragana Sinica* Root Extract In order to confirm a change in skin brightness according to the use of the test and control products, a visual evaluation on skin was made before use and in 4, 6 and 8 weeks after use.

The visual evaluation on a skin color of a test region was made by two experts on the basis of an intensity score table, which is a skin color evaluation reference table, wherein a brightness of skin color was evaluated by ranging from scores 1 (bright and transparent) to 10 (dark and dull), depending on the skin color. If there is any difference of evaluation between two investigators, a lower score was selected as an evaluation material. Table 15

TABLE 15

| Classification | Test Product | | Control Product | | Significance Probability of |
|---|---|---|---|---|---|
| | Score | Significance Probability | Score | Significance Probability | Test-Control Comparison |
| Test of within-subject effect | — | 0.000* | — | 0.697 | — |
| Before use | 3.174 ± 0.576 | — | 3.087 ± 0.793 | — | — |
| 4 weeks after use | 3.000 ± 0.739 | 0.046 | 3.043 ± 0.878 | — | 0.252 |
| 6 weeks after use | 2.826 ± 0.778 | 0.005[#] | 3.000 ± 0.953 | — | 0.108 |
| 8 weeks after use | 2.564 ± 0.752 | 0.002[#] | 3.130 ± 0.920 | — | 0.006[##] |

Figure 7:
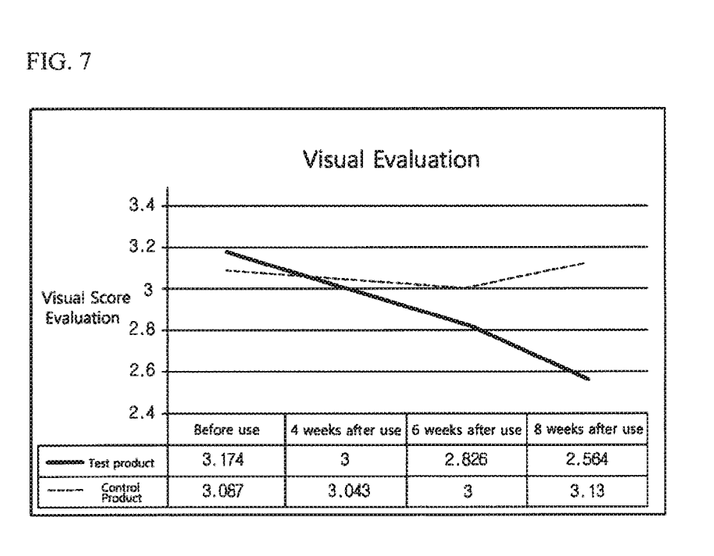
FIG. 7 shows results of a visual evaluation on skin color changes according to the application of the cosmetic composition comprising the fraction of *Caragana Sinica* root extract.

[#] $p < 0.017$ (=5%/3) Results of conducting a Friedman test as a non-parametric method and then a post-hoc test with a non-parametric test method according to a test of normality
[##] $p < 0.05$ Mann-Whitney U test results In the Table 15, data showed that the results of 23 subjects were indicated as an average±standard error (SE), wherein a degree of their changes was illustrated in graph in FIG. 7.

As seen in Table 15 and FIG. 7, scores of visual evaluations on whitening of the test product group made by experts were significantly decreased (significance probability <0.017) in 6 and 8 weeks after use in comparison with before use, and also showed a significant difference (significance probability <0.05) in 8 weeks after use in comparison with the control product. Accordingly, it was confirmed that the cosmetic composition comprising the fraction of *Caragana Sinica* root extract gave a benefit to a skin whitening from 6 weeks after use.

What is claimed is:

1. A skin whitening method, comprising applying a cosmetic composition to skin, wherein the cosmetic composition comprises: (a) an ethyl acetate fraction of an ethanol extract of *Caragana Sinica* root, wherein the ethyl acetate fraction comprises alpha-viniferin at a concentration of 4 µM to 8 µM as an active ingredient, and (b) a carrier, wherein the ethyl acetate fraction is present in an amount of 0.01 wt % to 10 wt % based on the total weight of the cosmetic composition, and wherein the alpha-viniferin has an IC50 of 7 uM on melanin production.

2. The method of claim 1, wherein the ethyl acetate fraction contains 0.1 wt % to 1 wt % of α-viniferin based on the total weight of the fraction.

* * * * *